United States Patent [19]

Wilcox et al.

[11] Patent Number: 5,801,046
[45] Date of Patent: Sep. 1, 1998

[54] *BACILLUS THURINGIENSIS* ISOLATES

[75] Inventors: David R. Wilcox, Lincolnshire; Robert A. Smith, Lindenhurst; Terry A. Benson, Waukegan, all of Ill.

[73] Assignee: Abbott Laboratories, Abbott Park, Ill.

[21] Appl. No.: 387,970

[22] Filed: Feb. 10, 1995

Related U.S. Application Data

[63] Continuation of Ser. No. 141,431, Oct. 21, 1993, abandoned, which is a continuation of Ser. No. 650,500, Feb. 5, 1991, abandoned.

[51] Int. Cl.$^6$ .................................................. C12N 1/20
[52] U.S. Cl. .............................. 435/252.5; 424/93.461
[58] Field of Search ............................. 435/243, 252.1, 435/252.5, 832; 424/93.461

[56] References Cited

U.S. PATENT DOCUMENTS

| | | | |
|---|---|---|---|
| 4,206,281 | 6/1980 | Goldberg | 435/242 |
| 4,695,455 | 9/1987 | Barnes et al. | 435/252.31 |
| 4,902,507 | 2/1990 | Morris et al. | 435/252.31 |
| 4,935,353 | 6/1990 | Burges et al. | 435/252.31 |
| 5,063,055 | 11/1991 | Burges et al. | 435/252.5 |
| 5,080,897 | 1/1992 | Gonzalez et al. | 435/252.5 |

OTHER PUBLICATIONS

Visser, B. et al. "A novel *Bacillus thuringiensis* gene encoding a Spodoptera exigua-specific crystal protein"; Journal of Bacteriology, vol. 172, No. 12, Dec. 1990, pp. 6783–6788.

Sanchis, V. et al. "Multiplicity of delta–endotoxin genes with different insecticidal specificities in *Bacillus thuringiensis* aizawai 7.29"; Molecular Microbiology, vol. 2, No. 3, 1988, pp. 393–404.

Hofte et al., Appl. & Environ. Microbiol., 54 (8), pp. 2010–2017 (Aug. 1988).

Prefontaine et al., Appl. & Environ. Microbiol, 53(12) pp. 2808–2814 (Dec. 1987).

Shimizu et al, Agric. Biol. Chem. 52(6), 1988, pp. 1565–1573.

*Primary Examiner*—Irene Marx
*Attorney, Agent, or Firm*—Andreas M. Danckers; Michael J. Ward

[57] ABSTRACT

Novel bacterial isolates of *B. thuringiensis* are disclosed which have enhanced toxicity with respect to previously resistant or insufficiently susceptible insect species, including, but not limited to, *Plutella xylostella*, *Spodoptera frugiperda* and *Spodoptera exigua*, as well as certain secondary pests such as *Trichoplusia ni*. Such isolates may be characterized by their possession of a particular subset of the genes coding for the various *B. thuringiensis* δ-endotoxin proteins and by a characteristic plasmid profile, or array, known to be associated therewith.

Also disclosed are a method for the efficient identification of such bacterial isolates utilizing generalized or, alternatively, gene-specific DNA probes; cloned or synthesized nucleotide sequences which are useful in the preparation of those probes; compositions containing an insecticidally effective amount of a bacterial isolate of the invention in combination with an acceptable carrier; and a method for the use thereof in the control or eradication of insect pests.

2 Claims, 1 Drawing Sheet

Figure 1
Agarose Gel Showing *B. thuringiensis* Extrachromosomal Elements (Plasmids)

12.2 –
3.0 –
2.0 –

1.0 –

BACILLUS THURINGIENSIS ISOLATES

This application is a continuation of U.S. Ser. No. 08/141,431, filed Oct. 21, 1993, now abandoned, which was a continuation of U.S. Ser. No. 07/650,500, filed Feb. 5, 1991, abandoned.

TECHNICAL FIELD

The present invention relates to organisms producing biological pesticides. More particularly, it pertains to novel strains of the bacterium *Bacillus thuringiensis* which are effective against certain insect species, as well as to methods for the preparation and use thereof.

BACKGROUND OF THE INVENTION

Insecticides have enjoyed widespread use in commercial agriculture, and have enabled an enormous increase in crop yields and product quality. Pesticides are also routinely used to control various insects, as for example flies or mosquitoes, when pest populations pose a nuisance or health hazard to humans or livestock. There is, however, an increasing awareness of environmental risks associated with the use of certain synthetic pesticides, including concern over the bioaccumulation of pesticides in the food chain or their detrimental effects on non-target organisms. Biological pesticides and especially natural biopesticides have therefore been of considerable interest to those seeking environmentally acceptable means of pest control.

The microorganism *B. thuringiensis* has long been recognized to be useful in the control of insect pests. The sporulating *B. thuringiensis* cell produces a class of compounds, formerly regarded as a single δ-endotoxin but now understood to comprise several distinct toxin proteins, which are concentrated in a crystalline protein inclusion body found in the endospore. Upon ingestion of the inclusion body by a susceptible insect larva and proteolysis in the insect gut, the endotoxin proteins are converted into active compounds which destroy the gut epithelium and ultimately the pest itself.

*B. thuringiensis* δ-endotoxins have accordingly been found to be useful as pesticides when applied in the form of lysates or other fermentation extracts of cultures of the microorganism. These toxins show remarkable activity against a variety of *Lepidoptera* species and other insects. However, *B. thuringiensis* preparations have proved to be of only limited value in combating insects such as those of the genera *Spodoptera* and *Plutella*, as well as various other lepidopteran pests. This toxicity of *B. thuringiensis* preparations against only certain pest species, or differential toxicity, is believed to be due to the expression of only certain endotoxin genes in any given *B. thuringiensis* variant, each toxin contributing in an unpredictable manner to the overall toxicity profile.

Numerous researchers have attempted to identify *B. thuringiensis* strains which have a broader or different spectrum of pesticidal activity, or to manipulate the *B. thuringiensis* genome to promote the expression of particular δ-endotoxins. Efforts directed to screening individual isolates for toxicity have led to the isolation of some previously unknown strains such as *B. thuringiensis* var. *tenebrionis*, dislosed by Krieg et al. in U.S. Pat. No. 4,766,203, issued Aug. 23, 1988, which strain is reportedly effective for combating Coleoptera. The use of conventional screening procedures to identify strains with new pesticidal activity, however, is time- and labor-intensive given the innumerable variants of *B. thuringiensis* that occur in nature.

Another approach has been to clone genes coding for *B. thuringiensis* δ-endotoxins and to re-arrange the *B. thuringiensis* genome in a beneficial way, or to introduce the cloned genes into new microbial hosts for expression. Herrnstadt et at., in U.S. Pat. No. 4,771,131, issued Sep. 13, 1988, describe the cloning of an M-7 toxin gene said to be suitable for expression in other microbes such as Pseudomonas and to thereby confer the ability to control beetles of the order Coleoptera. These methods, however, suffer from the drawback that the resulting organisms are subjected to increased regulatory scrutiny relative to organisms which occur naturally.

There is, therefore, a continued need for the identification of *B. thuringiensis* strains which display a broader or different spectrum of pesticidal activity. Ideally, such strains would be identified from among naturally occurring variants without the use of random screening methods.

SUMMARY OF THE INVENTION

Accordingly, the present invention comprises novel bacterial isolates of *B. thuringiensis* which have enhanced toxicity with respect to previously resistant or insufficiently susceptible insect species. These isolates can be employed against several insect species resistant to treatment with *B. thuringiensis* including, but not limited to, *Plutella xylostella* (diamondback moth), *Spodoptera frugiperda* (fall armyworm) and *Spodoptera exigua* (beet armyworm), as well as certain secondary pests such as *Trichoplusia ni* (cabbage looper). The bacterial isolates of the invention may be characterized by their possession of a particular subset of the genes coding for the various *B. thuringiensis* endotoxin proteins and by a characteristic plasmid profile or array known to be associated therewith.

The present invention also comprises a method for the efficient identification of such bacterial isolates, in which a generalized nucleotide probe may be used to establish, in a strain already known to have some toxicity to a particular insect pest, the identity of that strain's endotoxin genes. Next, gene-specific DNA probes are prepared for the detection of those endotoxin genes; these probes are then used to pre-screen *B. thuringiensis* strains to identify a set of variants which are capable of synthesizing the corresponding endotoxins. The variants thus selected may ultimately be subjected to further screening of a more conventional nature to obtain particular variants which display even higher levels of pesticidal activity.

Further comprised by the present invention are cloned or synthesized nucleotide sequences which are useful in the preparation of the gene-specific DNA probes of the invention. These sequences are determined by sequence analysis of the target genes of interest and in accordance with the degree of specificity desired. Where a generalized probe (i.e., one capable of recognizing multiple endotoxin genes) is required, a nucleotide sequence may be constructed which is based on a conserved region of the *B. thuringiensis* toxin genes. Alternatively, sequences which are unique to the various toxin genes may be used to prepare highly specific probes.

The present invention additionally comprises the use of bacterial isolates of the invention in the control or eradication of insect pests, as well as compositions containing an insecticidally effective amount of such an isolate in combination with an acceptable carrier.

BRIEF DESCRIPTION OF THE DRAWINGS

The present invention is described with reference to the attached drawing, in which FIG. 1 is a set of plasmid profiles for *B. thuringiensis* strain ABTS 1857 and several reference strains.

DETAILED DESCRIPTION OF THE INVENTION

In one aspect of the present invention, bacterial isolates of *Bacillus thuringiensis* are disclosed which are chosen from among available *B. thuringiensis* variants by a procedure which includes pre-screening for a selected subset of those genes coding for *B. thuringiensis* δ-endotoxin proteins. The isolates of the present invention possess differential toxicity towards particular insect species, and include isolates of *B. thuringiensis* variants which are toxic to pest species previously found to be resistant or insufficiently susceptible to *B. thuringiensis* insecticides.

Exemplary of the invention are strains effective against pests selected from the group consisting of *Spodoptera frugiperda, S. exigua, Plutella xylostella* and *Trichoplusia ni*. It is now found that these pest species may be controlled with an isolate of *B. thuringiensis* which expresses the cryIA(a), cryIA(b), cryIC and cryID genes and, optionally, which lackes the cryIA(c) gene. While not intending to be limited by theory, this gene complement is believed to account, at least in part, for the superior pesticidal activity of these strains. Moreover, the activity of these genes is believed to be related to their organization within the bacterial genome. A plasmid array, or profile, which is readily obtainable as for example by electrophoretic separation of bacterial plasmids, may serve to characterize the genetic architecture of a strain and thus serve as a further identifier of a bacterial isolate of the invention. A representative plasmid profile, obtained from *B. thuringiensis* ABTS 1857, is shown in FIG. 1.

A preferred example of the bacterial isolates of the present invention is the novel bacterial isolate *B. thuringiensis* ABTS 1857, described herein, which possesses the above-described gene complement and which demonstrates improved toxicity towards Plutella xylostella when compared to commercial *B. thuringiensis* strains. *B. thuringiensis* ABTS 1857, which is of the subspecies *aizawai*, was deposited under accession number SD-1372 with the American Type Culture Collection in Rockville, Md. on Oct. 11, 1990. (On Jul. 6, 1992, this deposit was converted to a patent deposit under the terms of the Budapest Treaty and was accorded accession number ATCC 69074). In addition to the plasmid profile of FIG. 1, strain ABTS 1857 is identifiable by the biochemical characteristics of Example 4 herein and by the display of flagellar serotype H-7 (identical to U.S. Department of Agriculture *B. thuringiensis* type strain HD-11), as well as the presence of at least three endotoxin gene-containing plasmids (shown by heat-curing.)

In another aspect of the present invention are disclosed biologically pure cultures of the above isolates. By "biologically pure culture" as used herein is meant a culture essentially free from biological contamination and having a genetic uniformity such that different subcultures taken therefrom will display substantially identical genotypes and phenotypes. Such cultures are useful in large-scale fermentation or, alternatively, as the starting material for well-known strain manipulation techniques. Accordingly, mutants, recombinants and genetically engineered variants which are derived from the isolates of the present invention, and cultures thereof, are regarded as being within the scope of the invention.

In yet another aspect of the present invention, a method is disclosed for isolating a strain of *B. thuringiensis* which is effective against a particular target pest species. The method comprises the steps of first identifying a combination of genes coding for endotoxin proteins, the presence or absence of which is determinative of toxicity towards a particular target pest; next, pre-screening or isolating from among available *B. thuringiensis* strains a set of variants which contain that combination of endotoxin genes; and then screening that set of variants to obtain a preferred isolate. The identification of particular endotoxin gene combinations, and the ability of the corresponding toxin complexes to produce differential toxicity against different target pests, may be accomplished by comparing the toxicity of strains which synthesize certain toxins with others which do not. If necessary, genes responsible for the production of toxins of interest may be selectively removed, as by heat curing, and the resulting strains tested for enhancement or diminution of toxicity.

Alternatively, desirable combinations of *B. thuringiensis* δ-endotoxin genes may be identified using a generalized nucleotide probe capable of hybridizing with all such genes. A number of toxin genes, including cryIA(a), cryIA(b), cryIA(c), cryIB, cryIC, cryID, cryIE, cryIIIA, cryIIIB, cryIVA, cryIVB, and cryIVC, have been identified, and partial or entire sequences thereof have been published, as for example by Schnepf et al in J. Biol. Chem., 260:6264–6272 (1985). It has been found that certain regions of these genes are highly conserved, permitting the preparation of a DNA probe which recognizes *B. thuringiensis* endotoxin genes in general. Such a generalized probe, when hybridized with the genome of a strain which through routine screening has been found to have some degree of toxicity towards a pest species of interest, may then be used to identify and characterize the endotoxin genes present in that type strain. These manipulations, as well as others which are useful in the practice of the present invention, may be accomplished using techniques which are well-known and can be found in references such as Maniatis et al., Molecular Cloning, A Laboratory Manual, Cold Spring Harbor Laboratory, 1982.

One example of a generalized probe, used to identify the genes cryIA(a), cryIA(b), cryIC and cryID which appear to confer improved toxicity characteristics upon *B. thuringiensis* , is the novel probe containing the sequence

ATCGCAGAGAGATGACTCTAACTGTGT-
TAGATATCGTTCCTCTATTTC CAAATTATGACCG
(SEQ ID NO:1).

Such sequences, when reported in the literature, may be prepared using standard procedures for the synthesis of polynucleotides. Alternatively, sequences may be cloned directly from known genes of interest. Related probes may be used as well; for example, fragments of the above sequence, which are sufficient in length to hybridize specifically with δ-endotoxins, are also suitable for use as generalized DNA probes of the present invention. It should be noted that here and elsewhere in this disclosure, nucleotide sequences are expressed in the conventional manner, namely, in the 5'-to-3' direction where A is adenine, G is guanine, C is cytosine and T is thymine.

Once a particular combination of endotoxin genes has been identified, the method of the invention provides for the isolation of a set of *B. thuringiensis* variants which contain exactly that combination of genes and are thus capable of producing the corresponding combination of endotoxin proteins. The isolation of variants may be accomplished by first determining a unique nucleotide sequence of a portion of each gene coding for each of the desired endotoxins, and then preparing a set of gene-specific nucleotide probes which are capable of hybridizing with those sequences. Such unique sequences are obtained from what have been described as highly variable (i.e., non-conserved) regions of the *B. thuringiensis* δ-endotoxin genes. As in the case of the generalized probes described above, the construction of gene-specific probes may in some cases be accomplished by reference to published nucleotide sequences. Alternatively, where sequence data are unavailable or where a new endotoxin gene has been identified, the genes of interest must be cloned or sequenced to a degree which permits identification of unique sequences useful for cloning or synthesis of the corresponding probe sequences.

Gene-specific probes which may be employed in identifying the δ-endotoxin genes of *B. thuringiensis*, such as those used in the preferred embodiment of the method of the present invention, may be constructed from nucleotide sequences which include the following:

ACAATGCTGAGCCAAGCAGCTGGAG-CAGTTTACACCTTGAGAGCT (SEQ ID NO:2) for identification of the cryIA(a) gene;

GACGGAGCCTATGAAAGCAATTCTTCTG (SEQ ID NO:3) for identification of the cryIA(b) gene;

GCTACGTCATTAGATAATCTACAAT-CAAGTGATTTTGGTTATTTTGAAA GTGCCAAT-GCTTTTACATCTTCATTAGGTAATATAG-TAGGTCTTAGAA ATTTTAGTGGGACTGCAGGAGTG (SEQ ID NO:4) for identification of the cryIA(c) gene;

GGATTTAGAGTTTGGGGGGGCACC (SEQ ID NO:5) for identification of the cryIC gene; and GCGCATACTCTTGCATCTGGTGCC (SEQ ID NO:6) for identification of the cryID gene.

These sequences may be used in their entirety, or may be shortened, lengthened or internally modified to obtain probes possessing the desired degree of homology to, and corresponding hybridization specificity for, the endotoxin genes sought to be identified. Moreover, it is anticipated that, as additional endotoxin genes and their respective unique sequences become known, or where certain genetic variants of known genes are found to confer desirable properties on *B. thuringiensis* strains containing them, new probes will be derived which may be employed without departing from the practice of the method of the present invention.

The above gene-specific probes, which may be labeled in any of a number of conventional ways to permit assessment of their binding, can then be used to rapidly and economically pre-screen all available strains of *B. thuringiensis*. This pre-screening may be carried out using well-known techniques such as replica plating, hybridization, autoradiography and the like. In this manner, one may easily select, from among the strains being tested, a set of variants which demonstrate a pattern of hybridization representative of the gene complement being sought. It should be noted in this respect that the method of the present invention may include pre-screening not only for the presence of particular endotoxin genes, but also for the absence of others found to inhibit or to have no discernable effect on the desired toxicity.

It is anticipated that the above isolation method of the invention, although described above in connection with the identification and pre-screening for *B. thuringiensis* δ-endotoxin genes, is equally well suited for the selection of sets of variant strains bearing other, non-toxin DNA sequences which nonetheless may be found to participate in the determination of differential toxicity. For example, should a regulatory gene or unexpressed sequence be identified which affects the quantity of endotoxins produced or the specificity of those toxins towards a target pest, sequence-specific nucleotide probes may be prepared and used to pre-screen naturally occurring *B. thuringiensis* variants for the presence or absence of such sequences. Consequently, by "genes" or "genes coding for endotoxin proteins" as used herein is meant not only DNA sequences expressed as endotoxins but also those sequences which regulate such expression or which, when expressed themselves, modify the toxicity profile of the *B. thuringiensis* strain containing them.

From among the variants selected by pre-screening, a preferred *B. thuringiensis* strain may be identified by conventional but small-scale screening for toxicity. The isolate ultimately selected may then be optimized for toxin production using known techniques of yield improvement or by the manipulation of the strain itself, such as by the production of mutants, recombinants or genetically engineered derivatives thereof. Such manipulation may also include the preparation of a preferred phenotype of the selected isolate, as for example a spo⁻ (asporogeneous) mutant which produces a toxin crystal but no spores. It will be appreciated, however, that the method of the invention may also be employed in an iterative fashion, and that the ultimate isolate may be used as the starting point for a new cycle of identifying genetic determinants of a particular toxicity profile, constructing the appropriate gene-specific or sequence-specific probes, and pre-screening *B. thuringiensis* strains at large for the presence of those determinants.

In another aspect of the present invention, compositions are disclosed comprising an insecticidally effective amount of a bacterial isolate of the invention, or an endotoxin obtained therefrom, in combination with an acceptable carrier. After identification and stabilization of a suitable *B. thuringiensis* variant according to the above methodology, large-scale fermentation may be carried out using media and fermentation techniques which are standard in the industry. The endotoxin crystals (together with the spores, from which the crystals are not readily separable) may then be separated from the fermentation broth and lyophilized or formulated in any of a number of well-known ways, including as a liquid concentrate, dry or wettable powder or suspension for spraying on or under foliage, and a granular preparation for application to soil. By "acceptable carrier" as used herein is meant an otherwise inert filler or excipient which confers upon the composition desirable storability, material handling and application characteristics; commonly-used carriers may include fillers, binders, surfactants, dispersants, adhesion agents and the like. A preferred example of a composition of the invention is one containing the isolate *B. thuringiensis* ABTS 1857 or a mutant, recombinant or genetically engineered derivative thereof.

In still another aspect of the present invention, a method for controlling insect pests is disclosed which comprises applying, to an area infested with said pests, an insecticidally effective amount of a bacterial isolate of the invention or an endotoxin obtained therefrom. By "insecticidally effective amount" as used herein is meant that amount of a bacterial isolate or endotoxin which is capable of substantially eradicating the target pest as measured, for example, by pest mortality or the absence of further crop damage. Numerous factors will affect the amount of bacterial isolate or endotoxin needed, including the method of application; the prevailing weather conditions such as temperature, humidity, rainfall and wind; the extent of pest infestation; the stage of growth of the target species and the like. Where the insects to be controlled are pests such as *Spodoptera frugiperda*, *S. exigua*, *Plutella xylostella* and *Trichoplusia ni*, a preferred embodiment of the pest-control method of the invention is one in which the active agent applied is a bacterial isolate of *B. thuringiensis* ABTS 1857 or a mutant, recombinant or genetically engineered derivative thereof.

The present invention will be better understood in connection with the following examples which should be regarded as illustratrations only, and not as limitations, of the invention.

EXAMPLE 1

General Methodology
Sample Preparation and Growth Conditions

Isolation of *B. thuringiensis* strains from soil was accomplished using procedures designed to favor the germination of *B. thuringiensis*-type bacilli over other microorganisms which include six to ten species of spore-forming bacilli as well as non-sporulating bacteria, yeast and fungi. A short heat treatment (80° C. for 10 minutes) was utilized to activate spores, after which the samples were rapidly subcultured on NSYM agar medium per Myers and Youseten 1980.

Colonies of *B. thuringiensis*-type bacilli were selected on the basis of colony morphology and growth characteristics typical of that species. Also, microscopic examination was used to identify the endotoxin protein crystal which differentiates *B. thuringiensis* from *Bacillus cereus*, a common soil bacterium which is otherwise morphologically and biochemically indistinguishable.

*B. thuringiensis* isolates for use in bioassays were grown in 250 ml culture flasks containing 50 ml Media 168 (18 g soy flour,0.3 g $MgSO_4 \cdot 7H_2O$, 0.7 g $K_2HPO_4$, 0/5 g $CaCO_3$, 1.0 ml 1% $FeSO_4 \cdot H_2O$, and 1.0 ml 1% $ZnSO_4$ in 1 liter deinonized water; autoclaved; approximately 2.5 ml sterile 20% glucose solution per 100 ml, added prior to use). Cultures were incubated for 72 hours at 28° C. with shaking at 250 rpm, after which 3 ml samples were dispensed into sterile 15 ml polypropylene tubes and frozen at −20° C. for later analysis.

Bioassay for Strain Toxicity

The toxicity of bacterial isolates was assayed in the laboratory by exposing larvae of pest species to an insect diet treated with varying quantities of the bacteria. Parallel dilution series of the test strain and of a reference bacterium were prepared, selecting ranges of concentrations (after initial pre-testing, if necessary) to obtain series mid-points at or near the respective $LD_{50}$s. To 36 ml aliquots of a conventional insect diet (principally agar, soy flour, solid nutrients and vitamin supplements) held liquid at 60° C. were added 4 ml of each dilution, including deinonized water standards. After mixing, each 40 ml sample of the treated diet was divided, while still hot, into six 1 ounce plastic cups and allowed to cool until the diet had solidified and had reached room temperature for at least 1 hour.

The samples were then infested with the pest species of interest, as for example with two second instar 2-day-old larvae in the case of *S. frugiperda*, by carefully placing larvae into each cup. The cups were individually covered and incubated for 64 to 68 hours in an environmental chamber (24-hour darkness, 28° C., 20–50% relative humidity). After incubation, the numbers of living and dead larvae were counted, and the results used for subsequent $LC_{50}$ analysis.

DNA Probe Preparation and Colony Hybridization

Generalized and gene-specific DNA probes for use in the method of the invention were prepared by synthesizing the desired oligonucleotides on an automated Applied Biosystems 380B® 3-column DNA synthesizer, using the standard β-cyanoethanol phosphoramidite chemistries provided with that device. The resulting oligonucleotides were end-labelled using $\gamma$-$AT^{32}P$ (Amersham) and employing the procedure of Maxam and Gilbert (1980) for 5' end-labelling with T4 polynucleotide kinase.

Bacterial isolates were prepared for hybridization with the above probes by serial dilution and plating, after which single colonies were placed with sterile toothpicks into 96-well microtiter dishes containing liquid LB media (5 g NaCl, 10 g bactotryptone and 5 g yeast extract per liter) and incubated for at least 4 hours at 28° C. Using a 96-prong metal stamp, the culture arrays were multi-replicated by transfer to 1.2 micron nylon hybridization membranes placed over solid LB agar plates and to a master bioassay plate, and allowed to incubate at 28° C. for approximately 16 hours.

The resulting colonies were then protoplasted by floating the filters for one hour, colony side up, on a 10 mg/ml lysozyme solution in TES buffer (30 mM Tris-HCl, 5 mM EDTA, 50 mM NaCl). After protoplasting, the filters were washed by rocking them gently in an excess first of denaturing buffer (0.5M NaOH, 2.5M NaCl) for 30 minutes with one change of buffer, and then of neutralizing buffer (0.5M Tris, pH 7.0, 3.0M NaCl) also for 30 minutes with one change of buffer. The filters were briefly air-dried and placed in an 80° C. oven for at least 1 hour before prehybridization and hybridization according to the method of Southern (1975).

The hybridized filters were washed two times, each for 1 hour, with citrate buffer (0.1% SDS w/v, 30 mM sodium citrate, 0.3M NaCl, adjusted to pH 7.0 with HCl) at 58° C. for 1 hour and air-dried on blotting paper. Hybridizations were then evaluated by overnight exposure of the filters, in a −70° C. freezer, to Kodak X-Omat® AR film using an intensifying screen, and by subsequent development and analysis of the film.

EXAMPLE 2

Identification of Preferred Endotoxin Combinations

*B. thuringiensis* δ-endotoxin genes connected with toxicity against beet and fall armyworm and diamondback moth were identified as follows: Several observations of variable toxicity against *Spodoptera exigua* and *Trichoplusia ni* on the part of *B. thuringiensis* HD-1 variants led to the finding that the loss of a toxin gene, as determined by Southern blot, resulted in significantly reduced Spodoptera kills. The loss of the corresponding gene, later identified as cryIA(b), was confirmed by Southern blot analysis. Independently, cloned cryIA(b) and cryIA(c) genes were expressed in *Escherichia coli*, from which isolated granules and extracts were prepared which also exhibited marked differential toxicity against these pest species. Together, the studies suggested that cryIA(b) gene was essential for toxicity, but that cryIA (c) might be altogether unnecessary.

A derivative strain of *B. thuringiensis* HD-1 was then prepared by heat-curing, and purified crystals from that strain were assayed for toxicity against larvae of *S. frugiperda* and *T ni*. The derivative strain, which contained the cryIA(a) and cryIA(b) genes but lacked cryIA(c), demonstrated substantially improved activity against *S. frugiperda*. Accordingly, gene-specific DNA probes for cryIA(a), cryIA (b) and cryIA(c) were prepared and used to screen *B. thuringiensis* soil isolates for variants having an identical gene complement.

Approximately twenty such variants were identified and bioassayed for activity against *S. frugiperda*. One strain in particular, designated ABTS 5803, was identified as being highly active, displaying twice the toxicity towards that species as the reference strain HD-1. Strain ABTS 5803 was therefore analyzed by treatment with a generalized DNA probe patterned after a conserved region of the then-known B. thuringiensis endotoxin genes, and was found, using Southern analysis, to contain two new genes in addition to cryIA(a) and cryIA(b). Upon cloning and sequencing, these genes were identified as cryIC and cryID. Further studies using plasmid heat-curing showed the genes to be located on at least three separate plasmids, with cryIC and cryID located together if not adjacently. Derivatives of ABTS lacking one or more of these genes were found to have attenuated toxicities; consequently, the combination of genes cryIA(a), cryIA(b), cryIC and cryID (exclusive of cryIA(c)) was chosen for use in subsequent pre-screening.

EXAMPLE 3

Identification of B. thuringiensis Variants and Preparation of Strain ABTS 1857

A bacterial isolate representative of the present invention was obtained as follows: Using gene-specific probes for the above combination of four endotoxin genes, B. thuringiensis single-colony soil isolates were pre-screened until approximately 100 variants possessing those genes were identified. These in turn were tested for activity against S. frugiperda. One variant, isolated from soil collected in Ephriam, Wis. and identified as strain ABTS 5686, was found to have activity superior to all others, and to produce a toxin/spore complex having three times the toxicity towards S. frugiperda of the reference strain B. thuringiensis HD-1.

Again using gene-specific probes, the genotypic purity of strain ABTS 5686 was verified by examining single-colony isolates of that strain for retention of all four desired endotoxin genes and thus of all gene-bearing plasmids. Thirty-three colonies with a full and, therefore, apparently stable gene complement were pooled and re-designated strain ABTS 1857. Further examination of plasmid stability at 34° C. (instead of the usual culture temperature of 28° C.) confirmed stability of the genome, with a cryIA(b) gene loss of only 2% over 72 hours at this elevated temperature. B. thuringiensis strain ABTS 1857 was then more fully characterized and tested for pesticidal activity as described below.

EXAMPLE 4

Characterization of B. thuringiensis ABTS 1857

Differential growth and metabolic characteristics of B. thuringiensis ABTS 1857 were evaluated in accordance with Bergey's Manual of Systematic Bacteriology, vol. 2, 1986, pp. 1104–1129, with deviations from that procedure as indicated below. The following characteristics (in which X=positive, 0=negative, V=variable and T=trace response) were noted:

| | |
|---|---|
| Cell diameter >1.0 micron | X |
| Spores round | 0 |
| Sporangium swollen | 0 |
| Parasporal crystals | X |
| Catalase | X |
| Anaerobic growth | X |
| Voges-Proskauer test | X |
| pH in V-P broth <6.0 | X |
| Acid from | |
| D-glucose | X |

-continued

| | |
|---|---|
| L-arabinose | V |
| D-xylose | V |
| D-mannitol | V |
| Gas from glucose | 0 |
| Hydrolysis of | |
| Casein | X |
| Gelatin | X |
| Starch | X |
| Utilization of | |
| Citrate | X |
| Propionate | X |
| Degradation of tyrosine | 0 |
| Deamination of phenylalanine | 0 |
| Egg-yolk lecithinase | X |
| Nitrate reduced to nitrite | X |
| Formation of | |
| Indole | 0 |
| Dihydroxyacetone | 0 |
| NaCl and KCl required | 0 |
| Allantoin or urate required | 0 |
| Growth at pH | |
| 6.8 nutrient broth | X |
| 5.7 | X |
| Growth in NaCl (%) | |
| 0 | X |
| 2 | X |
| 5 | X |
| 7 | 0 |
| 10 | 0 |
| Growth at (°C.) | |
| 5 | 0 |
| 10 | T |
| 15 | X |
| 20 | X |
| 25 | X |
| 30 | X |
| 35 | X |
| 40 | X |
| 45 | X |
| 50 | X |
| 55 | 0 |
| Growth with lysozyme present | X |
| Autotropic with $H_2$ and $CO_2$ | 0 |

In the detection of lecithinase, a solid agar medium was used in place of the liquid medium recommended in Bergey, above, so that estimation of lecithinase production was more precise. For auxotrophic growth analysis, Gaspak® jars and gas generators (BBL) were used to provide the appropriate gas environment, and growth was rated after 3 days of incubation at 20°–30° C.

Antibiotic sensitivities, when assayed per the criteria of S.O.P. 047T-12-034A of National Committee for Clinical Laboratory Standards relative to the response of the control organism Staphylococcus aureus, were as follows (where R=resistant and S=sensitive):

| | |
|---|---|
| Gentamycin | S |
| Kanamycin | S |
| Erythromycin | S |
| Clindamycin | S |
| Penicillin | R |
| Ampicillin | R |
| Cephalothin | R |
| Vancomycin | S |
| Chloramphenicol | S |
| Trimethoprim/ Sulfamethoxazole | S |

EXAMPLE 5

Preparation of Plasmid Profiles

A plasmid profile of *B. thuringiensis* strain ABTS 1857 was obtained using a procedure adopted from Gryczan et al. (1978) as modified by Shivakumar et al. (1986), and compared to profiles of *B. thuringiensis kurstaki* HD-1 and to two type strains of *B. thuringiensis* subsp. *aizawai*, HD-11 and HD-133, as follows: Cultures of the strains were grown in 50 ml polypropylene centrifuge tubes containing 20 ml LB for approximately 16 hours at 28° C. with shaking (250 rpm). Cells were harvested by centrifugation at 4800×g for 10 minutes at 4° C., and washed twice with 1 ml TES buffer (30 mM Tris, pH 7.5, 5 mM EDTA, 40 mM NaCl) before pelleting in a microcentrifuge after each wash. The supernatant was aspirated and the pellets resuspended in 180 µl sucrose medium (25% sucrose, 0.1M NaCl, 0.05M Tris, pH 7.5). The samples were mixed thoroughly and 20 µl lyxozyme (50 mg/ml in sucrose medium) added without further mixing. After incubation at 37° C. for 1 hour, the cells were lysed by adding 48 µl 5M NaCl, 12 µl 0.5M EDTA, and 260 µl 2% SDS in 0.7M NaCl to each sample and mixing slowly by inverting the tubes twice, followed by further incubation for 10 minutes at 68° C. The samples were then chilled for 1 hour in an ice bath, and chromosomal DNA and cell debris removed by microcentrifugation for 15 minutes while maintaining a temperature of 4° C. Approximately 300 µl of supernatant was gently removed from each sample with a blunted eppendorf pipette tip, guarding against contact with the sample interface to avoid DNA shearing, and transfered to a clean eppendorf tube.

The samples were then treated with 33 µl 3M sodium acetate and 670 µl ethanol at 4° C. to precipitate the plasmid DNA, and held at −20° C. for 18 hours before being microcentrifuged at 4° C. for 15 minutes. The ethanol was decanted and the tube edges blotted dry, and the pellets dried by centrifuging under vacuum for 30 minutes at room temperature. Each pellet was then covered with 200 µl TES buffer and left undistrubed for 15 minutes before resuspension by gentle pipetting using a blunt eppendorf pipette tip and flicking with a fingertip. 2 µl each of RNase A (10 mg/ml) and T1 RNase (100 U/ml) were added to each sample, and the samples incubated in a 37° C. waterbath for 1 hour. After adding 20 µl Proteinase K (10 mg/ml), each sample was incubated for an additional 2 hours.

Proteases were removed from the samples by phenol extraction using 200 µl buffered phenol (8-hydroxyquinolone added to 0.1%; extracted with one wash of 1M Tris, pH 8, and two washes of 0.1M Tris, pH 8, to produce a pH of 7.6) and brief mixing for 10 seconds. Each sample was then microcentrifuged for 3 minutes and the aqueous phase transferred to a fresh eppendorf tube. An equal volume (200 µl) chloroform:isoamyl alcohol (24:1 v/v) was added, and the samples mixed and centrifuged as before. The aqueous phase was removed and again precipitated with the addition of 1/10th volume 3M sodium acetate (20 µl) and 2.5 volumes ethanol (0.5 ml) at 4° C., and the samples held at −20° C. for 1 hour. The samples were then pelleted, dried, and resuspended in TES buffer as before.

Gel separations were conducted using a Pulsewave® 760 switcher (Bio-Rad) and bridge type gel beds, 10×15 cm which were plugged at each end with 1.5% agarose made in TBE buffer (8 mM Tris base, 89 mM boric acid, 2.5 mM EDTA, pH 8.3). Agarose gels (0.8%), made in TBE buffer, were poured to a depth of approximately 4 mm and fitted with 1.5×7 mm gel combs. The gels, kept at 4° C., were run at 80 volts for 1 hour and then covered with plastic film and the voltage decreased to 50 volts for 26 hours. Waveform parameters were "Field Inversion, Normal Run" with an initial A time of 9 seconds and a final A time of 60 seconds. The start ratio was 3 and the run time set to 26 hours.

The finished gels were stained with approximately 0.6% ethidium bromide for 30 minutes and destained for 15 minutes in water, before being photographed with back illumination under short wave UV light. A combination of two Tiffen® filters (25-red and 16-orange) were used, with Polaroid 667 film being exposed for 20 seconds at f22.

The resulting plasmid profile of strain ABTS 1857 is shown in FIG. 1 as lane 3, with lane 1 containing molecular weight markers having the indicated relative molecular weights (in mDa). Plasmid profiles of strains HD-1, HD-133 and HD-11 are shown as lanes 2, 4 and 5, respectively. It was noted in the case of strain ABTS 1857 that five plasmid bands migrated behind the chromosomal band and ten migrated behind, with one of the ten being partially obscured by the chromosomal smear. Of the remaining nine, two migrated close together as a doublet. It was observed that the plasmid profile of ABTS 1857 was unique and clearly discernable from those of the three reference strains.

EXAMPLE 6

Activity of *B. thuringiensis* ABTS 1857 Against Target Pests

Greenhouse and field testing was conducted to determine the efficacy of a bacterial isolate of the invention in controlling significant lepidopteran insect pests of vegetable crops, and in particular the pests *Plutella xylostella* (tested in the field) and *Spodoptera exigua* (tested in the greenhouse, after artificially infesting each plant with 20 2nd-instar, lab-reared larvae). A variety of crop species were used. The isolate, *B. thuringiensis* ABTS 1857, was prepared as a technical grade powder and tested using a randomized complete block experimental design with 6 to 8 replications. Standards for comparison were a *B. thuringiensis kurstaki* HD-1 technical powder, prepared in identical manner, and DiPel® 2× WP (Abbott), a commercial *B. thuringiensis* pesticide. The pesticide preparations were applied in the greenhouse with an airbrush sprayer at rates ranging from 0.5 to 4.8 mg/ml (with each plant receiving 2 ml spray), and in the field with a $CO_2$-pressurized backpack sprayer at rates of from 0.125 to 1.0 pounds per acre, expressed in each case as technical powder equivalents.

Activities of the preparations were evaluated based on post-treatment insect larval mortality or population reduction, and crop damage estimates where appropriate. Data were recorded no earlier than 3 days after treatment, and typically at 5- to 7-day intervals where multiple applications were applied in seasonal trials. Representative results of these tests are shown in Table 1 below, where defoliation was rated on a scale of 0 to 4, with 4 being complete defoliation.

TABLE 1

Larval Control of *Spodoptera exigua* and *Plutella xylostella*

| Target Pest | Crop | Treatment | Amount | % Mortality | Defoliation |
|---|---|---|---|---|---|
| *S. exigua* | Beet | 1857 | 0.5 | 89 | 0.68 |
| | | | 1.0 | 99 | 0.36 |
| | | | 2.0 | 100 | 0.0 |

TABLE 1-continued

Larval Control of *Spodoptera exigua* and *Plutella xylostella*

| Target Pest | Crop | Treatment | Amount | % Mortality | Defoliation |
|---|---|---|---|---|---|
| | | HD-1 | 0.5 | 84 | 0.81 |
| | | | 1.0 | 95 | 0.68 |
| | | | 2.0 | 96 | 0.13 |
| | | DiPel® | 2.4 | 45 | 2.16 |
| | | | 4.8 | 67 | 1.15 |
| *S. exigua* | Collards | 1857 | 1.2 | 97 | 0.15 |
| | | | 2.4 | 100 | 0.04 |
| | | HD-1 | 1.2 | 78 | 0.75 |
| | | | 2.4 | 91 | 0.44 |
| | | DiPel® | 2.4 | 61 | 0.78 |
| | | | 4.8 | 73 | 0.74 |
| *P. xylostella* | Cauli-flower | 1857 | 0.125 | 48 | — |
| | | | 0.5 | 92 | — |
| | | HD-1 | 0.125 | 40 | — |
| | | | 0.5 | 48 | — |
| | | DiPel® | 1.0 | 53 | — |
| *P. xylostella* | Rape-seed | 1857 | 0.125 | 62 | — |
| | | | 0.5 | 78 | — |
| | | HD-1 | 0.125 | 23 | — |
| | | | 0.5 | 40 | — |

These data show the test strain, ABTS 1857, to have significantly enhanced activity against pyrethroid- and *B. thuringiensis*-resistant diamondback moth larvae and beet armyworm when compared to the HD-1 standard strain. Additionally, the test strain was found to provide commercially acceptable crop protection against non-resistant diamondback moth, cabbage looper and imported cabbageworm, against which it showed activity at least equal to that of standard *B. thuringiensis* products.

The isolates and other aspects of the present invention are described above in connection with *B. thuringiensis* strains which are principally of the subspecies *kurstaki* and *aizawai*. It should be noted, however, that the techniques disclosed herein are applicable to the identification and use of novel *B. thuringiensis* isolates of any type or serovar.

What is claimed is:

1. A biologically pure bacterial strain of *Bacillus thuringiensis* having all the identifying characteristics of *Bacillus thuringiensis* ABTS 1857.

2. A biologically pure bacterial culture of a *Bacillus thuringiensis* ABTS 1857.

* * * * *

UNITED STATES PATENT AND TRADEMARK OFFICE
CERTIFICATE OF CORRECTION

PATENT NO. : 5,801,046
DATED : September 1, 1998
INVENTOR(S) : Wilcox et al.

It is certified that error appears in the above-identified patent and that said Letters Patent is hereby corrected as shown below:

Column 10, line 41, change "Autotropic" to --Autotrophic--.

Column 10, line 49, change "after 3 days" to --after 3 and 6 days--.

Signed and Sealed this

Second Day of March, 1999

Attest:

Q. TODD DICKINSON

*Attesting Officer*      *Acting Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 61 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:1:

ATCGCAGAGA GATGACTCTA ACTGTGTTAG ATATCGTTCC TCTATTTCCA AATTATGACC    60

G    61

( 2 ) INFORMATION FOR SEQ ID NO:2:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:2:

ACAATGCTGA GCCAAGCAGC TGGAGCAGTT TACACCTTGA GAGCT    45

( 2 ) INFORMATION FOR SEQ ID NO:3:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:3:

GACGGAGCCT ATGAAAGCAA TTCTTCTG 28

(2) INFORMATION FOR SEQ ID NO: 4:

( i ) SEQUENCE CHARACTERISTICS:
    ( A ) LENGTH: 120 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO: 4:

GCTACGTCAT TAGATAATCT ACAATCAAGT GATTTGGTT ATTTGAAAG TGCCAATGCT 60

TTTACATCTT CATTAGGTAA TATAGTAGGT CTTAGAAATT TTAGTGGGAC TGCAGGAGTG 120

(2) INFORMATION FOR SEQ ID NO:5:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:5:

GGATTTAGAG TTTGGGGGGG CACC 24

(2) INFORMATION FOR SEQ ID NO:6:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:6:

GCGCATACTC TTGCATCTGG TGCC 24